United States Patent

Assa et al.

Patent Number: 5,906,609
Date of Patent: May 25, 1999

[54] METHOD FOR DELIVERING ENERGY WITHIN CONTINUOUS OUTLINE

[75] Inventors: Shlomo Assa, Encinitas; Jeffrey Rideout, Santee; Scott Paterson, Vista, all of Calif.

[73] Assignee: Sahar Technologies, San Diego, Calif.

[21] Appl. No.: 08/792,355

[22] Filed: Feb. 5, 1997

[51] Int. Cl.⁶ .................................................. A61B 17/36
[52] U.S. Cl. .................. 606/9; 606/18; 606/11; 279/121.85
[58] Field of Search ................... 606/9, 11, 12; 607/89; 219/121.6, 121.61, 121.76, 121.8, 121.85

[56] References Cited

U.S. PATENT DOCUMENTS

| | | |
|---|---|---|
| 4,733,660 | 3/1988 | Itzkan . |
| 4,750,486 | 6/1988 | Butler et al. . |
| 4,945,914 | 8/1990 | Allen . |
| 4,973,848 | 11/1990 | Kolobanov et al. . |
| 5,336,217 | 8/1994 | Buys et al. . |
| 5,344,434 | 9/1994 | Talmore . |
| 5,474,528 | 12/1995 | Meserol . |
| 5,474,549 | 12/1995 | Oritz et al. . |
| 5,501,680 | 3/1996 | Kurtz et al. . |
| 5,531,740 | 7/1996 | Black . |
| 5,544,651 | 8/1996 | Wilk . |
| 5,546,214 | 8/1996 | Black et al. . |
| 5,558,666 | 9/1996 | Dewey et al. . |
| 5,588,428 | 12/1996 | Smith et al. . |
| 5,595,568 | 1/1997 | Anderson et al. . |
| 5,653,706 | 8/1997 | Zavislan et al. ............ 606/9 |
| 5,658,323 | 8/1997 | Miller ........................ 607/89 |
| 5,662,644 | 9/1997 | Swor ........................... 606/9 |

FOREIGN PATENT DOCUMENTS

| | | |
|---|---|---|
| 1260116 | 9/1989 | Canada . |
| 0753285 A1 | 1/1997 | European Pat. Off. . |
| 1347142 | 10/1987 | U.S.S.R. . |
| WO 82/0426 | 12/1983 | WIPO . |

Primary Examiner—Lee Cohen
Assistant Examiner—Roy Gibson
Attorney, Agent, or Firm—David J. Weitz; Wilson Sonsini Goodrich & Rosati

[57] ABSTRACT

A method is provided for delivering energy to a selected area on a surface. The method includes forming a visually continuous outline on the surface, positioning the visually continuous outline such that the outline surrounds an area to be treated with energy, and delivering energy within the area surrounded by the visually continuous outline. The method may be used to deliver energy to any surface, including surfaces which need to be exposed prior to the delivery of energy. Examples of surfaces that may be treated with energy using the method and apparatus of the present invention include, but are not limited to skin, an exposed area of internal tissue such as muscle or fat tissue, and a surface in an oral cavity such as gum tissue or a tooth enamel. Examples of particular applications to which the method may be applied include, but are not limited to skin surface ablation, hair removal, hair implantation, gum ablation and disinfection, tooth enamel cleaning, fat tissue ablation for breast reduction, evaporation of severely burned tissue, drilling a hole in heart muscle, heating tissue for pain reduction, and the ablation of tumors within the body.

28 Claims, 13 Drawing Sheets

METHOD FOR DELIVERING ENERGY WITHIN CONTINUOUS OUTLINE

BACKGROUND OF THE INVENTION

1. Field of the Invention

The present invention relates to a method and apparatus for delivering energy to a surface. More specifically, the present invention relates to a method and apparatus involving the formation of a visually continuous outline around an area of a surface within which energy is to be delivered.

2. Description of Related Art

A wide variety of skin abnormalities exist for which treatment is commonly sought to remove the abnormality. Examples of such skin conditions include dermatologic acne, scars (most commonly due to acne), xanthomas, and unwanted skin discoloration. Examples of skin discolorations include freckles, age or liver spots, birthmarks, malignant melanomas, nevi (melanocytic, epidermal, vascular, and connective tissue), lentigines (brown spots on the skin or mucous membrane) and tatoos. In addition, discoloring abnormalities may be due to vascular lesions which are caused by an abundance of enlarged blood vessels. Common examples of discolorful vascular lesions are "port wine" stain birth marks, telangiectasis, a colored spot formed most commonly on the skin by a dilated capillary or other small blood vessel, and hemangioma, a highly visible benign tumor composed of well-formed blood vessels and classified as capillary or cavernous.

A variety of methodologies have been developed for treating skin abnormalities including, for example surgical excision, skin grafting, dermabrasion, saliabrasion, cryosurgery and laser surgery. One particular class of these methodologies involves the treatment of skin with an energy source, most commonly a laser or an RF electrode which causes thermal damage or necrosis to the skin.

A major problem associated with the treatment methods involving the delivery of energy to the skin to cause thermal damage or necrosis is controlling where energy is being delivered to the skin as well as the amount of energy that is delivered to particular areas of the skin. A need therefore exists for a method and device for delivering energy to the skin which provides the user of the method and/or device with the ability to control where energy is delivered to the skin and how much. At the same time, the method and device should be easy for the user to use so that the skin can be treated safely, accurately, rapidly and economically. These and other objectives are provided by the device and method of the present invention which is described herein.

SUMMARY OF THE INVENTION

An apparatus is provided for delivering energy to a selected area on a surface. The apparatus includes an outlining mechanism which receives light from a light source and directs an aiming beam to a surface, an energy source direction modulator which receives energy from an energy source and directs the energy to the surface, and a controller which causes the outlining mechanism to move the aiming beam relative to the surface to form a visually continuous outline around an area of the surface and causes the energy source direction modulator to deliver energy within the area formed by the visually continuous outline. In one embodiment, the apparatus includes an operator selectable activation mechanism. In this embodiment, continuous activation of the activation mechanism is required in order to deliver energy.

A hand held dermoablation apparatus is also provided which includes a handpiece, a distal end for resting the apparatus against a of a patient, an outlining mechanism which receives light from a light source and directs an aiming beam to the patient's skin, an energy source direction modulator which receives energy from an energy source and directs the energy to the patient's skin, and a controller which causes the outlining mechanism to move the aiming beam relative to the patient's skin to form a visually continuous outline around an area of the patient's skin and causes the energy source direction modulator to deliver energy within the area formed by the visually continuous outline.

A method is also provided for delivering energy to a selected area of a surface. According to the method, a visually continuous outline is formed on the surface. The visually continuous outline is positioned on the surface such that the outline surrounds an area to be treated with energy. Energy is then delivered within the area surrounded by the visually continuous outline.

A method is also provided for delivering energy to a selected area of a surface which includes the step of activating an activation mechanism which causes energy to be delivered within the area surrounded by the visually continuous outline. According to this method, continuous activation of the activation mechanism is required in order to deliver energy.

A method is also provided for ablating selected areas of skin on a patient. According to the method, a visually continuous outline is formed on a patient's skin. The visually continuous outline is positioned such that the outline surrounds an area of skin to be ablated. Energy is then delivered to the area of skin surrounded by the visually continuous outline.

In the apparatus and methods of the present invention, the visually continuous outline can have a plurality of shapes including polygons (square, diamond, rectangle, triangle, pentagon, hexagon, heptagon, and octagon), circles and ellipses. These shapes can be predetermined by the apparatus or programmed into the apparatus by the operator. The visually continuous outline can also have a plurality of sizes which can be predetermined by the apparatus or fully adjustable within a size range.

The apparatus and method may be used to perform a variety of medical procedures. For example, the apparatus and method can be used to ablate a surface layer of skin, preferably less than about 0.05 mm thick, more preferably less than about 0.03 mm thick. Energy can also be directed to the surface in a pattern adapted for performing dermoablation, for removing hair from an area of skin or for creating holes in skin into which hair follicles can be implanted.

The controller used in the apparatus preferably includes a feedback system for controlling the outlining mechanism, energy source direction modulator as well as how and when energy is delivered. For example, the feedback system can be used to disable the delivery of energy when an error in an operation of the outlining mechanism or energy source direction modulator is detected by the feedback system. The feedback system can be used produce an error signal when an error in an operation of the outlining mechanism or energy source direction modulator is detected by the feedback system. The controller can also include software for controlling the size, shape and placement of the aiming beam and energy, the software being stored as RAM data and as ROM data. The feedback system can be used to compare the RAM data to the ROM data prior to operation of the apparatus and disable the delivery of energy if the RAM data does not match the ROM data. The feedback system can also monitor the amount of power delivered to the apparatus and disable the delivery of energy when the amount of power delivered to the apparatus falls below a predetermined level.

BRIEF DESCRIPTION OF THE FIGURES

FIG. 4A illustrates the step of directing an aiming beam to a surface such that the aiming beam forms a visually continuous outline around an area of the surface.

FIG. 4B illustrates the step of treating the outlined area with energy where the visually continuous outline is not produced while energy is directed to the surface.

FIG. 4C illustrates the step of treating the outlined area with energy where the visually continuous outline is produced while energy is directed to the surface.

FIGS. 7A–7D illustrate a method for performing dermoablation according to the present invention.

FIG. 7A illustrates an area of skin outlined on a patient's face.

FIG. 7B illustrates the ablation of the area of skin outlined in FIG. 7A.

FIG. 8A illustrates an outlined area of skin containing hair follicles.

FIG. 8B illustrates the ablation of the area of skin outlined in FIG. 8A.

FIG. 8C illustrates skin which has been treated repeated times to form a continuous mosaic of adjacent energy treated areas.

FIG. 8D illustrates the step of extending the continuous mosaic of adjacent energy treated areas by ablating the area outlined in FIG. 8C.

FIG. 9A illustrates outlining an area of skin.

FIG. 9B illustrates the ablation of the area of skin outlined in FIG. 9A.

FIG. 9C illustrates hair follicles being implanted into the ablated areas shown in FIG. 9B.

FIG. 9D illustrates skin which has been treated repeated times to form a continuous mosaic of adjacent energy treated areas.

FIG. 9E illustrates the step of extending the continuous mosaic of adjacent energy treated areas by ablating the area outlined in FIG. 9D.

DETAILED DESCRIPTION

Figure 1:
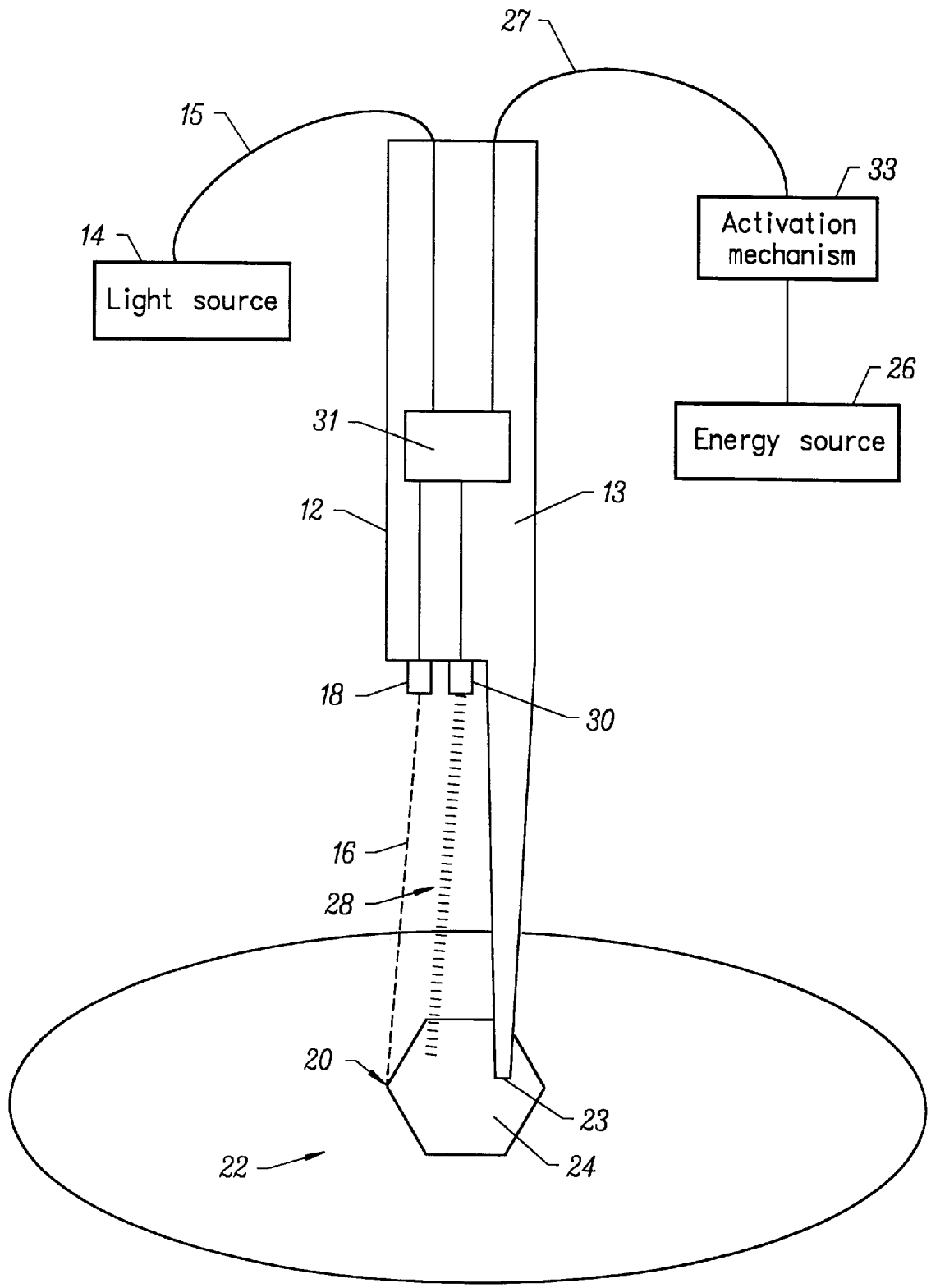
FIG. 1 illustrates an apparatus according to the present invention.
Figure 2:
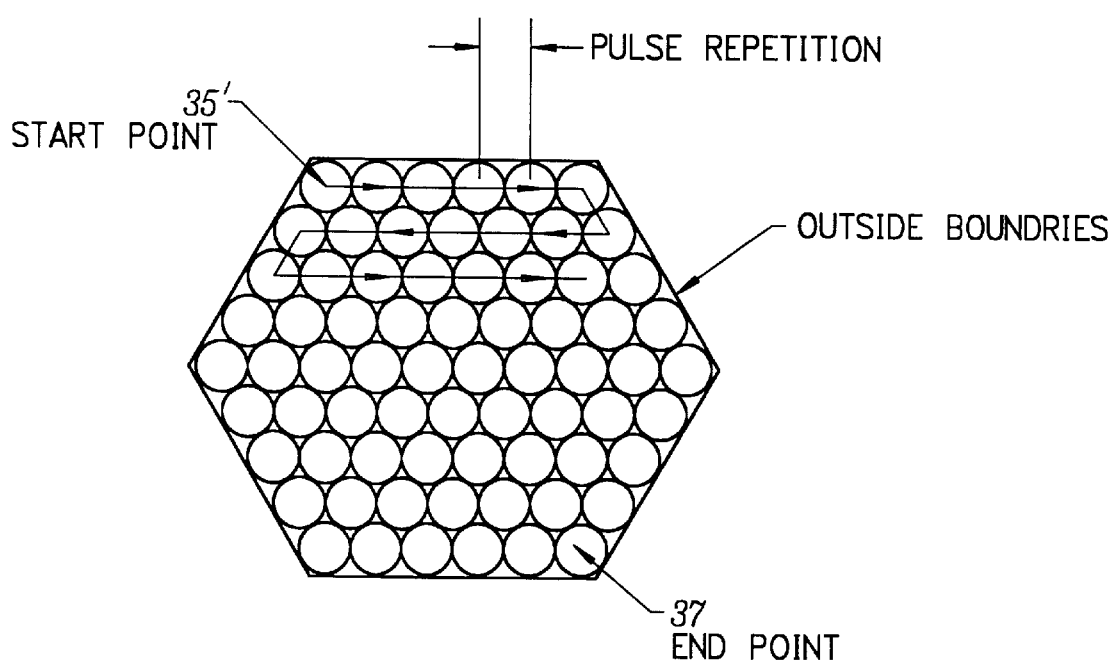
FIG. 2 illustrates a typical scanning motion geometry for a hexagonal area.

The present invention relates to a method and apparatus for delivering energy to a selected area on a surface where a visually continuous outline is formed around the selected area. This visually continuous outline identifies to the operator of the apparatus an area within which energy will be delivered. By forming a visually continuous outline around the selected area prior to delivering energy, the operator is able to accurately visually identify the area of the surface to which energy will be delivered before the energy is delivered. By being able to visualize the area that will be treated prior to the delivery of energy, the safety and accuracy of the method and apparatus is improved as compared to previous methods and devices.

A further aspect of the method and apparatus relates to the inclusion of an operator selectable activation mechanism which requires continuous activation by the operator in order to deliver energy. By requiring continuous activation for energy to be delivered, the operator is able to discontinue the delivery of energy by merely releasing the activation mechanism. As a result, the operator has a rapid and simple mechanism by which to stop the delivery of energy, thereby further improving the safety of the method and apparatus.

In general, the apparatus and method may be used to deliver energy to any surface, including surfaces which need to be exposed prior to the delivery of energy. Examples of surfaces that may be treated with energy using the method and apparatus of the present invention include, but are not limited to skin, an exposed area of internal tissue such as muscle or fat tissue, and a surface in an oral cavity such as gum tissue or a tooth enamel. Examples of particular applications to which the method and apparatus may be applied include, but are not limited to skin surface ablation, hair removal, hair implantation, gum ablation and disinfection, tooth enamel cleaning, fat tissue ablation for breast reduction, evaporation of severely burned tissue, drilling a hole in heart muscle, heating tissue for pain reduction, and the ablation of tumors within the body.

This invention is particularly important for use in applications where one needs to carefully control the area of a surface to which energy is applied. One such class of applications are dermatology procedures involving the treatment of selected areas of the skin with energy. Accordingly, the present invention is intended to encompass all forms of dermatology methods and apparatuses which include the application of energy to a desired area of skin. For example, energy may be used to ablate an upper layer of the skin (dermoablation), to remove hair from the skin, or to create holes within the skin into which hair follicles may be implanted. In these and other dermatology procedures, it is important that the location on the skin where energy is delivered be carefully controlled. Otherwise, unwanted damage can occur due to an area of tissue being exposed to energy that should not be treated (e.g., the eye) or due to an area being treated with too much energy, thereby causing scarring.

One embodiment of the invention is illustrated in FIG. 1. In this embodiment, the apparatus 12 includes a handpiece 13, an external light source 14 used to produce an aiming beam 16, a light conduit 15 for conveying light from the external light source 14 to the handpiece 13, an outlining mechanism 18 for moving the aiming beam 16 relative to a surface 22 to form a visually continuous outline 20 around an area 24 of the surface 22, an external energy source 26, an energy conduit 27 for conveying energy from the external energy source 26 to the handpiece 13, and an energy source direction modulator 30 which directs energy 28 from the handpiece 13 to different locations within the area 24 outlined on the surface 22.

The handpiece 13 is used by the operator to adjust the position of the visually continuous outline 20 on the surface 22 and hence where energy is delivered on the surface. The handpiece 13 may also include a distal end 23 which the operator positions against the surface, the distal end assisting in the operator's positioning of the visually continuous outline 20. When light energy is used, the light energy can be focused at a distance adjacent the distal end 23 of the handpiece 13.

Also included in the apparatus 12 is a controller 31 which is connected to the outlining mechanism 18, the light source 14, the energy source 26 and the energy source direction modulator 30. The controller 31 can be used to control the shape of the outline formed by the outlining mechanism 18. The controller 31 can also be used to control the energy source direction modulator 30 so that energy is delivered within area 24 outlined on the surface 22.

The controller 31 is preferably designed to operate the outlining mechanism 18 and energy source direction modulator 30 under feedback control, i.e., where the actual position of the aiming beam and/or energy is detected and fed back to the controller which adjusts the operation of the outlining mechanism 18 and energy source direction modulator 30 in response. If a predetermined error in the position of the aiming beam and/or energy is exceeded, the controller can be designed to interrupt the operation of the apparatus. The apparatus can also include a mechanism for providing the operator with an audible or visible signal that an error has occurred. In one embodiment of the controller, software used to control the size, shape and placement of the aiming beam and energy is stored in RAM, a non-volatile memory device and is redundantly stored in erasable ROM. The controller compares the RAM data to the ROM data prior to operation. If the ROM and RAM data do not match, the controller prevents the operation of the apparatus and signals the existence of a software error to the operator.

The controller 31 can also be used to control when and how energy is delivered to the surface. For example, the controller 31 can control energy intensity, spot size, and the scan speed of the energy source direction modulator 30. The controller 31 can also control whether energy is delivered in a continuous or pulsed manner. When pulses of energy is used, the controller can also be used to control the duration of each pulse.

The controller can also be used to monitor the amount of power being supplied to the apparatus. Low power can interfere with the proper operation of data processing operations in the apparatus. As a safety feature, the controller can be designed to discontinue the delivery of energy when power to the apparatus drops below a predetermined minimum acceptable level. The apparatus can also include a mechanism for providing the operator with an audible or visible signal that the power has dropped below the minimum acceptable level.

The controller preferably includes a microprocessor for performing the above-described operation. The use of a microprocessor provides increased control, precise placement, and homogeneous application of energy to the surface. Because of the normally tedious nature of applying single spot laser energy over large areas, a microprocessor controlled scanning system improves the safety of the device by decreasing fatigue experienced by the physician during a procedure. The high bandwidth design of the system offers scanner capabilities previously unavailable in any application other than $CO_2$ soft tissue, extending the safety and effectiveness improvements to a broader range of procedures.

As also illustrated in FIG. 1, the apparatus includes an operator selectable activation mechanism 33 which the operator activates in order to cause energy to be delivered from the apparatus. The operator selectable activation mechanism 33 is illustrated in FIG. 1 as a footswitch which the operator steps on to activate the apparatus. However, it should be understood that the operator selectable activation mechanism 33 can be incorporated into the apparatus in any manner by which the operator selectable activation mechanism 33 can be conveniently operated. For example, when the apparatus includes a handpiece 13, the operator selectable activation mechanism 33 can be incorporated onto the handpiece 13, for example, as a depressible button.

The operator selectable activation mechanism 33 is preferably designed to require continuous activation by the operator in order to deliver energy. For example, as illustrated in FIG. 1, the operator selectable activation mechanism 33 can be a footswitch which must be continuously depressed in order for energy to be delivered, release of the footswitch causing the delivery of energy to be discontinued.

The operator selectable activation mechanism 33 is preferably connected in series between the energy source 26 and the handpiece 13 such that energy is only delivered from the handpiece 13 when the activation mechanism 33 is being continuously activated by the operator. By requiring continuous activation, delivery of energy can be interrupted simply by discontinuing activation (e.g., letting go of a button or footswitch) as opposed to having to activate another mechanism (e.g., pressing a button) to deactivate the apparatus. This greatly increases the safety of the device by simplifying the system by which the delivery of energy is discontinued.

Figure 3:
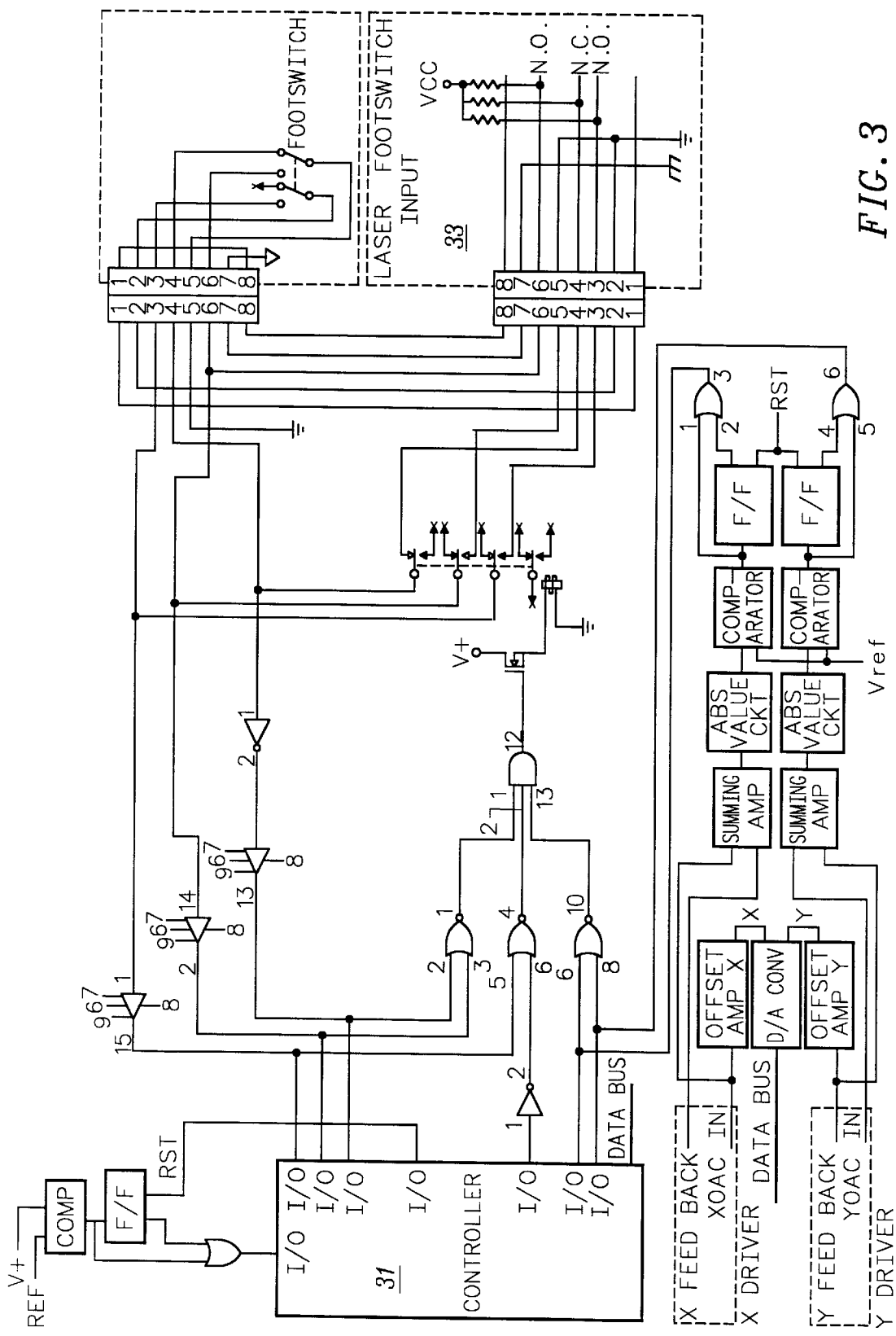
FIG. 3 illustrates a schematic for an embodiment of a controller system which may be used in an apparatus of the present invention.

A schematic illustrating an embodiment of controller system including an operator selectable activation mechanism 33 is illustrated in FIG. 3. In this embodiment, initial activation of the activation mechanism 33 serves to signal the controller 31 to initiate delivery of energy to the surface. When activated, the activation mechanism 33 forms a link between the energy source 26 and the handpiece 13 to allow energy to pass therethrough. When initially activated, the energy source direction modulator 30 is instructed to move at the appropriate step increment and frequency, rastering in X and Y axes, until the pattern defined by the aiming beam is filled in by treatment spots or emission. FIG. 3 illustrates a typical scanning motion geometry for a hexagonal area with a start point 35 and an end point 37. Once a scan is completed, the controller 31 disables the delivery of energy regardless of whether the activation mechanism 33 is activated. Depending on the mode of operation selected, the operator will either have to release the activation mechanism before pressing it again to initiate another scan cycle (single pass mode), or continue to hold the activation mechanism closed and wait for a predetermined period of time for another scan cycle to initiate (repeat mode).

In one embodiment, the apparatus is capable of producing a plurality of different outline area shapes and sizes. The apparatus is preferably capable of producing outlines of at least three different shapes and of at least three different sizes for a particular shape. According to this embodiment, the controller directs the outlining mechanism to produce one of the plurality of different outline area shapes and sizes. The controller also directs the energy source direction modulator to deliver energy within the outlined area. Hence, when a different outlined area size or shape is selected, the controller causes the energy source direction modulator to direct energy within the selected outlined area.

Figure 4A:
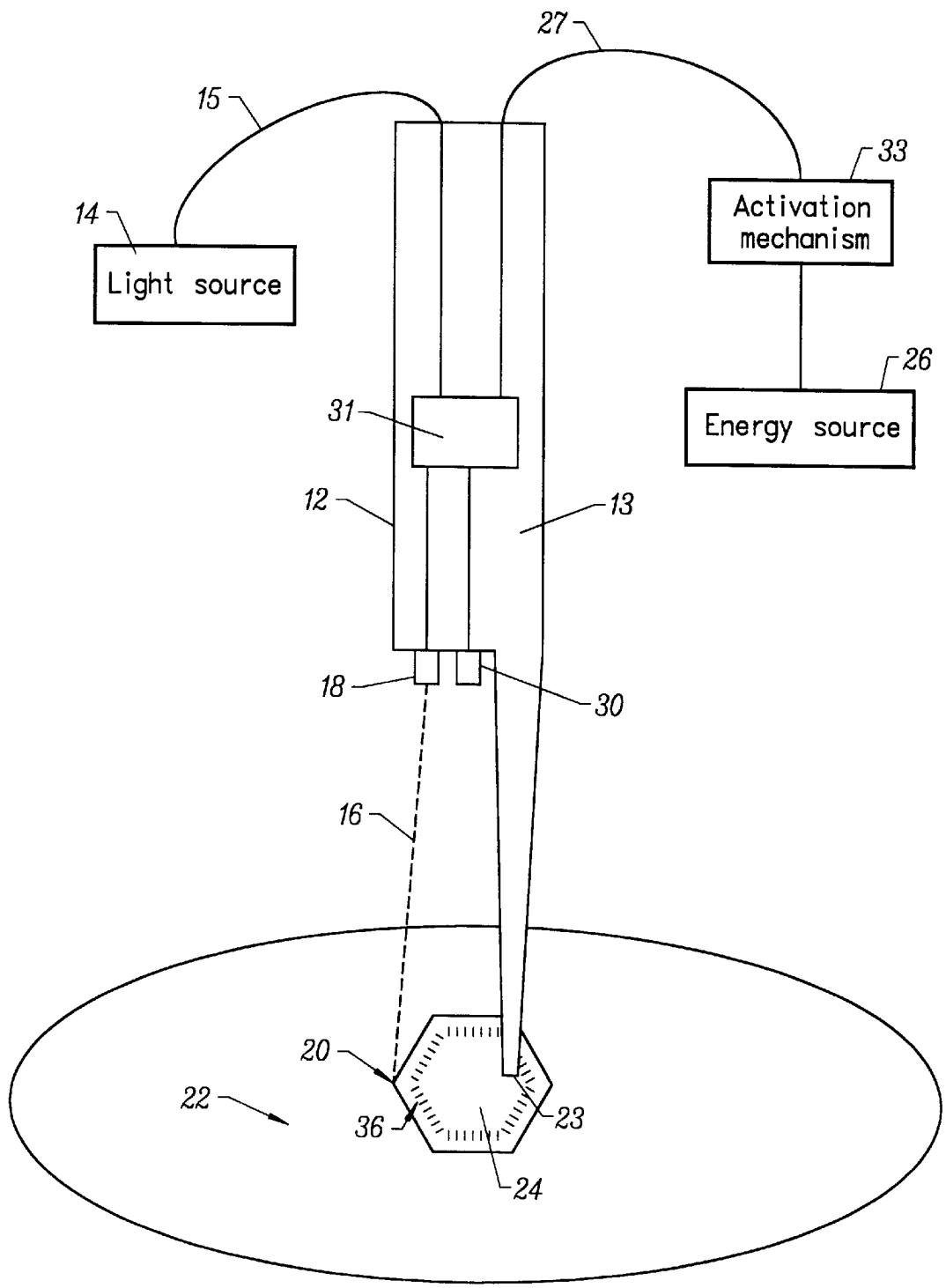
FIGS. 4A–C illustrate a method for treating a surface with energy according to the present invention.
Figure 4B:
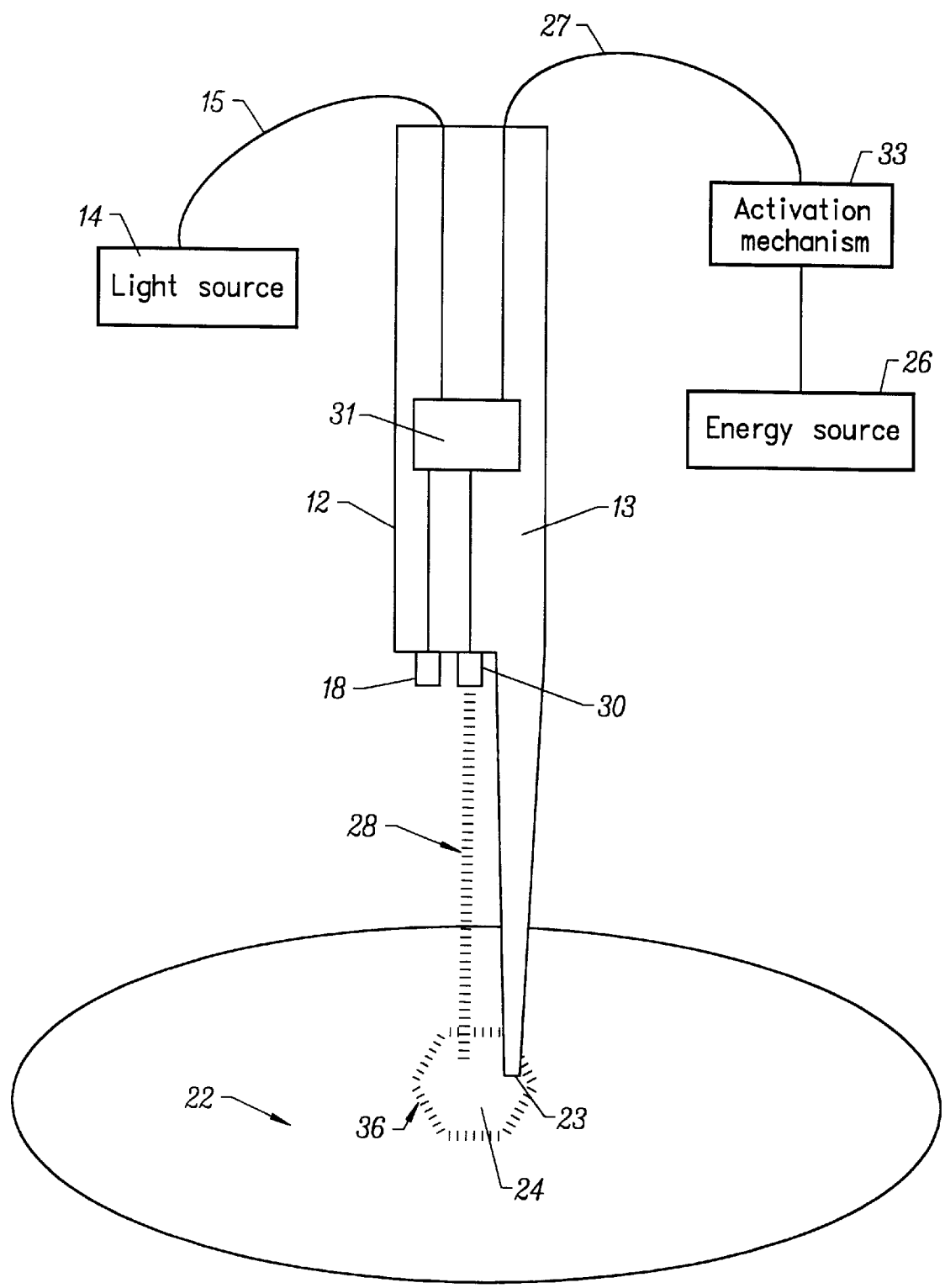
Figure 4C:
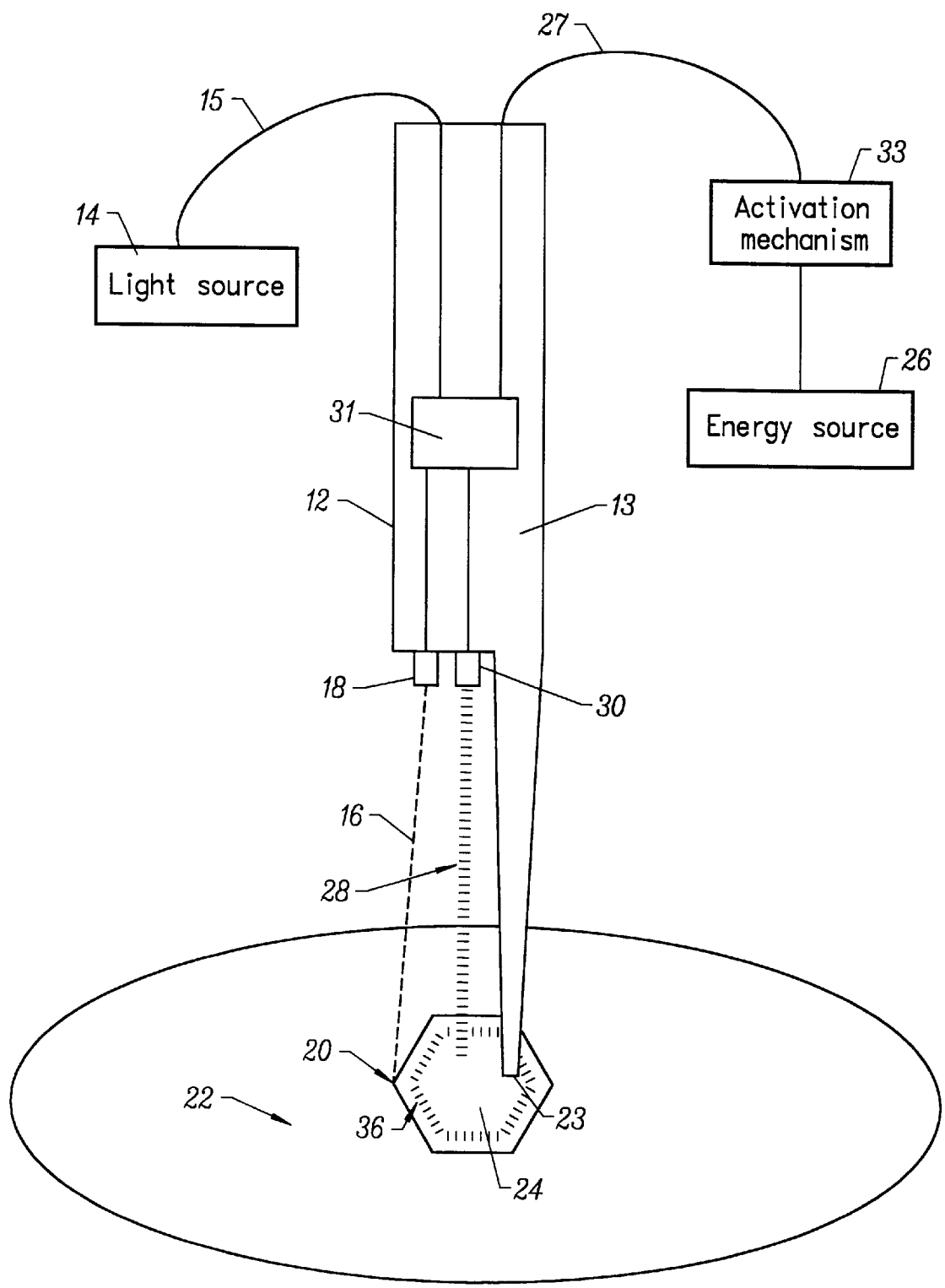

FIGS. 4A–C illustrate a method according to the present invention for delivering energy to a surface within an area identified by a visually continuous outline. According to a first step of the method, illustrated in FIG. 4A, an aiming beam 16 is directed to a surface 22 such that the aiming beam 16 forms a visually continuous outline 20 around an area 24 of the surface 22. The particular size and shape of the visually continuous outline that is formed is preferably selectable by the operator. Then, by adjusting the position of the visually continuous outline 20 on the surface 22 so that the outline surrounds an area 36 of the surface 22 which the operator wishes to treat with energy, the operator can selectively deliver energy to the desired area 36. The visually continuous outline 20 thus serves as a guide which clearly identifies to the operator where energy from the energy source will be delivered on the surface and enables the operator to accurately control the position of energy delivery.

Once the visually continuous outline 20 is positioned in the desired location on the surface, energy 28 is directed to the surface 22. In one embodiment, illustrated in FIG. 4B, the visually continuous outline 20 is not produced while energy 28 is directed to the surface 20. Alternatively, as illustrated in FIG. 4C, the visually continuous outline 20 is produced while energy 28 is directed to the surface 20. It is also envisioned that partial or intermittent outlines alternately may be formed while energy is directed to the surface.

The visually continuous outline used in the method and apparatus of the invention may be formed by a light source which forms an aiming beam and an outlining mechanism which moves the direction of the aiming beam such that the perimeter of an area on a surface appears to be continuously illuminated. As used in this application, the term "visually continuous outline" is intended to encompass any illumination of a perimeter of an area such that the perimeter appears to be illuminated at the same time to the naked eye. By illuminating the perimeter of the area to be treated, the user can directly visualize the area to be treated without having to approximate. The perimeter is preferably illuminated by a continuous line. However, the perimeter may also be illuminated by a series of spots and/or lines which surround the area.

The light source used to form the aiming beam may be any light source which produces a beam of light which can be sufficiently focused to form a visually continuous outline on a surface. It is generally preferred that a collimated light source such as a laser be used to form the aiming beam in view of the narrow beam diameters that can be generated. In one embodiment, the light source used to form the aiming beam is also used as the energy source. In one embodiment, the light source used to form the aiming beam also includes a mechanism which adjusts the diameter of the beam forming the outline on the surface.

According to the present invention, the outlining mechanism is used to adjust the direction of the aiming beam relative to the surface in order to form an outline around an area on the surface. In general, an outline is formed by causing a scanner to move a laser beam with a visible light emission repeatedly along a path at a frequency greater than can be discerned by the human eye, for example 30–50 times per second. As a result, the entire path appears to be continuously illuminated.

Methods for forming a visually continuous outline using a scanner and light source are known in the art. One approach is to divide an outline path into a series of points. Galvanometric motors can be used to move the light source from point to point in a continuous cycle. The galvanometric motors are preferably free-floating (no-springs) and are preferably operated under feedback control by the controller, allowing for very high bandwidths.

In one embodiment of the invention, the apparatus can produce outlines of one or more predetermined shapes including polygons (e.g., square, diamond, rectangle, triangle, pentagon, hexagon, octagon), circles and ellipses. The apparatus may also be designed so that the size of the area outlined is fully adjustable within a particular area size range. Accordingly, one embodiment of the method of the present invention includes the step of selecting one of the predetermined sizes and shapes for the visually continuous outline. In one embodiment, the outlined area has a size between about 9 mm$^2$ and 2500 mm$^2$.

The apparatus may also be programmable such that the operator can instruct the outlining mechanism as to the shape of the area around which the outline is to be formed. The ability to program the outline mechanism to provide a desired outlining pattern is particularly useful for the removal of skin tumors, tatoos and the treatment of other areas where the shape of the area to be treated varies on a case by case basis and where it is important to accurately control the treatment area. Programming the desired outlining pattern into the apparatus can be performed by a variety of methods known in the art. For example, the operator can employ a JoyStick to draw an outline which can be saved into memory. Alternatively, a computer mouse can be used to design an outlining pattern.

A variety of different forms of energy may be used with the method and apparatus of the present invention. Examples of such forms of energy include, but are not limited to electromagnetic energy, such as visible light, ultraviolet light, RF energy, microwaves and ultrasonic energy and thermal energy. When the energy source is visible light, the light may be coherent or non-coherent light. Coherent light is generally preferred because it is more reproducible and enables the energy source to be controlled more precisely. Examples of coherent light sources include lasers, such as excimer (351 nm), argon (488, 514 nm), Frequency doubled YAG (532 nm), ruby (694 nm), Nd:Yag (1060 nm), and CO$_2$ (10,600 nm) lasers.

When the energy source is a laser light source, the apparatus can be adapted to be used with multiple wavelengths of light. For example, the apparatus may be designed to be readily converted for use with different wavelengths by changing any wavelength specific reflectors and/or transmissive optics employed in the apparatus.

Collimating and focusing optics may be incorporated into the apparatus as is necessary to achieve laser light spots of a desired size and intensity. In one embodiment, the laser energy spots formed by the apparatus have a diameter between about 200 $\mu$m and 5 mm.

The form of energy used in a particular method or apparatus according to the present invention depends on the surface to be treated and the type and amount of energy which is needed to treat the particular surface. The form of energy used should also be focusable within the outlined area with the desired degree of accuracy. In some cases, it may be necessary for the energy to be focused onto a very small area, for example, in order to remove individual hair follicles. In other cases, it may be acceptable for the energy to be less focused and be delivered broadly over the area outlined. In one embodiment, the energy is focused within an area having a diameter between about 200 μm and 5 mm as it is delivered.

The location on the surface to which the energy is directed is controlled by an energy source direction modulator which is capable of moving the location on the surface where energy is applied. In addition to being coupled to the energy source, the energy source direction modulator is also coupled to the outlining mechanism through the controller so that the energy source direction modulator directs energy within the area outlined. As a result, changing the size and/or shape of the area outlined also serves to change the size and/or shape of the area treated with energy.

Figure 5:
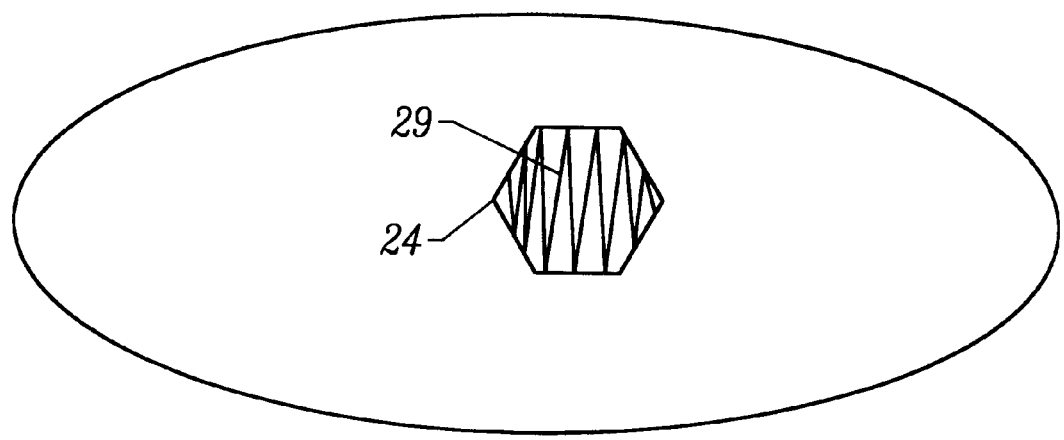
FIG. 5 illustrates energy being distributed substantially uniformly over an area of a surface.
Figure 6:
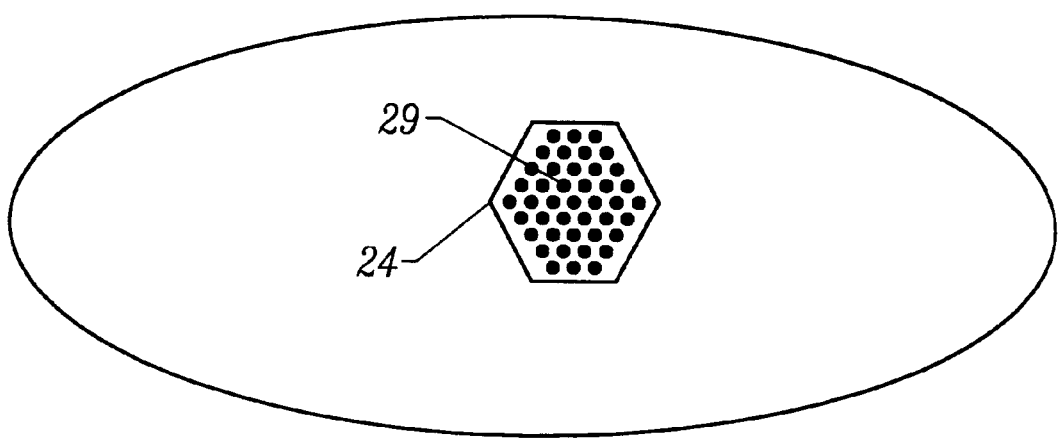
FIG. 6 illustrates energy being distributed in desired pattern within an outlined area.

The energy source direction modulator may be designed to direct energy over a desired pattern within the outlined area. For example, in one embodiment, the energy source and energy source direction modulator may direct energy over substantially all of the outlined area. For example, as illustrated in FIG. 5, energy may be rastered over area 24 (energy treated surface 29) with energy being continuously provided so that energy is substantially uniformly distributed over the area 24 of the surface 20 being treated. Alternatively, as illustrated in FIG. 6, energy may be delivered in a desired pattern within the outlined area 24 (energy treated surface 29).

When laser energy is used as the energy source, the energy source direction modulator may be attached to the handpiece or in some cases, to a flexible wave guide if the laser utilizes one. Laser energy enters the energy source direction modulator through an entry aperture.

Galvanometric motors may be used in the energy source direction modulator to move the energy source within the outlined area. The galvanometric motors are preferably free-floating and are preferably operated under feedback control by the controller. In one embodiment, two orthogonally mounted galvanometric motors are resident in the optical path inside the energy source direction modulator. Each motor has a mirror, with wavelength specific coatings, permanently mounted on the end of the motor shaft at a 45 degree angle with respect to an entry aperture. As the motor rotates the first axis mirror about the shaft, the energy is reflected to the other axis mirror, which reflects the energy thru an output aperture, creating a 2 dimensional image. By using the two motors in this manner, virtually any 2 dimensional shape can be imaged on a surface.

Due to the wide angle of travel provided by the galvanometric motors, a large outlined area can be treated with energy. The bandwidth capabilities of the galvanometric motors and control circuits also provide a wider range of pulsed laser repetition rates. While previous devices have had a maximum scan frequency of 200 Hz, the system of the present invention can have scan frequencies of up to 4 kHz.

In one embodiment, energy is delivered continuously to the surface as the energy source direction modulator adjusts the position of energy delivery. Alternatively, energy can be delivered non-continuously to the surface, for example in a pulsed pattern.

For a pulsed laser emission, the coordination of the energy pulses is performed on a timing baseline. During an energy pulse, the energy direction modulator keeps the energy focused on a single location within the area. Then, between energy pulses, the energy direction modulator redirects the energy so that energy is delivered to the next desired location. Since the duration of each pulse and the time between pulses are each generally constant, movement of the energy source by the scanner from point to point is generally performed on a fixed time basis. In addition, the time required for the energy direction modulator to direct the energy to the next desired location is generally small relative to the time between pulses. As a result, the energy direction modulator spends most of its time keeping the energy focused on a given location.

After energy has been delivered over a desired area of the surface, the delivery of energy is discontinued. Meanwhile, the outlining mechanism continues to produce an outline.

Figure 7A:
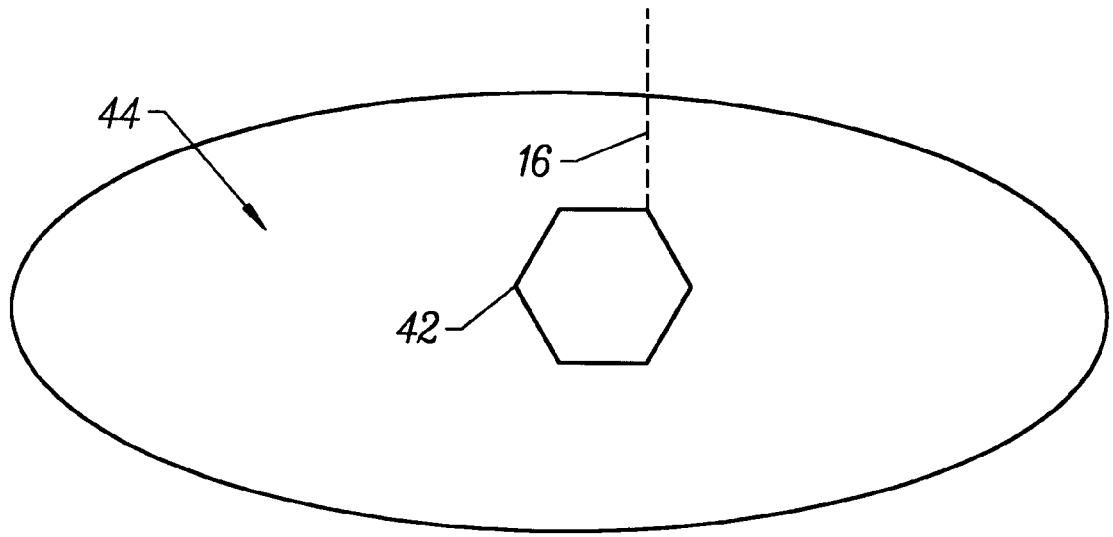
Figure 7B:
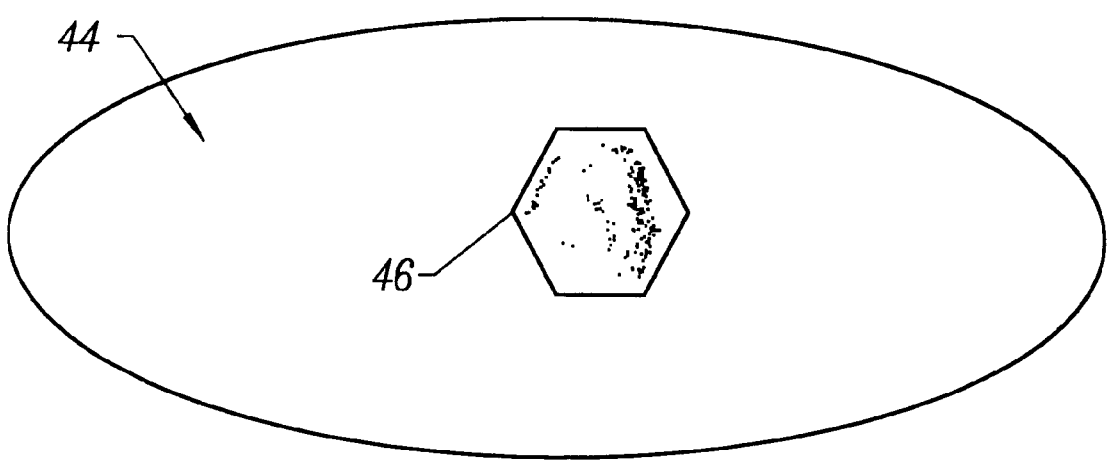

Illustrated in FIGS. 7A–7D is a method for performing dermoablation according to the present invention. As illustrated in FIG. 7A, an area 42 is outlined on a patient's skin 44. As illustrated in FIG. 7B, the area of skin 42 outlined in FIG. 7A is ablated with a laser. Area 46 corresponds to ablated skin. The procedure illustrated in FIGS. 7A and 7B may be repeated numerous times in order to ablate large areas of the skin. When repeating the steps illustrated in FIGS. 7A and 7B, it is generally preferred to outline and ablate areas adjacent to previously ablated area in order to form an ablation pattern over a larger area.

When ablating areas of skin which are larger than the outlined area, it is also generally preferred that the outlined area have a shape which is capable of forming a continuous mosaic of energy treated areas when a plurality of those shapes are laid next to each other. For example, a patient's skin can be ablated repeated times according to the steps illustrated by FIGS. 7A and 7B such that a continuous mosaic of adjacent energy treated areas is formed. The continuous mosaic is extended by outlining an area adjacent the energy treated areas and then ablating the adjacent area.

When the apparatus and method of the present invention are used to ablate an area of skin, the energy must be of a sufficient intensity to ablate the skin. However, the energy should also be selected so that it does not ablate tissue too far beneath the surface of the skin, generally about 0.03 mm–0.05 mm. Parameters which influence the depth of penetration include the pulse energy, pulse duration, size of the energy pulse on the skin, and the nature of the tissue being treated.

Figure 8A:
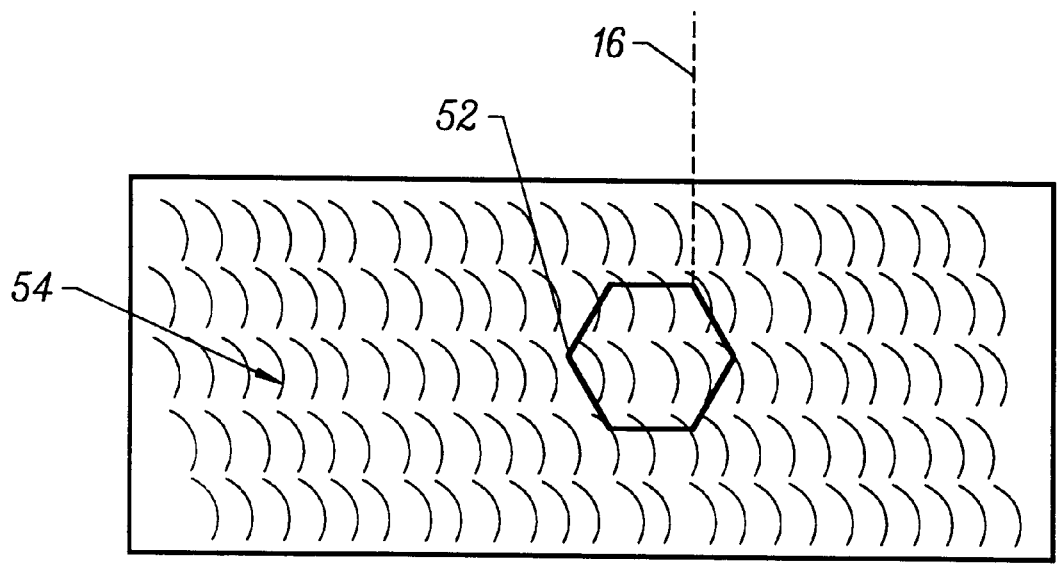
FIGS. 8A–D illustrate a method for removing hair according to the present invention.
Figure 8B:
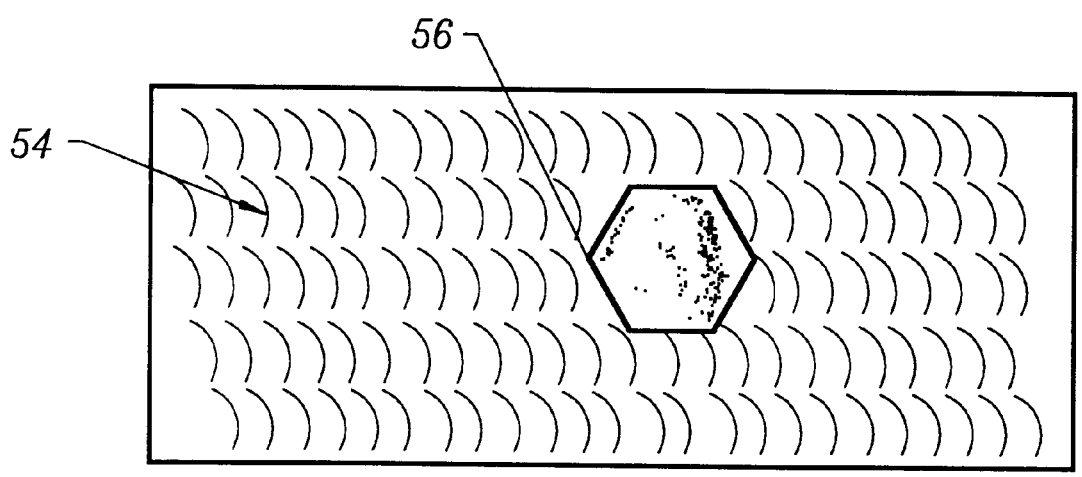
Figure 8C:
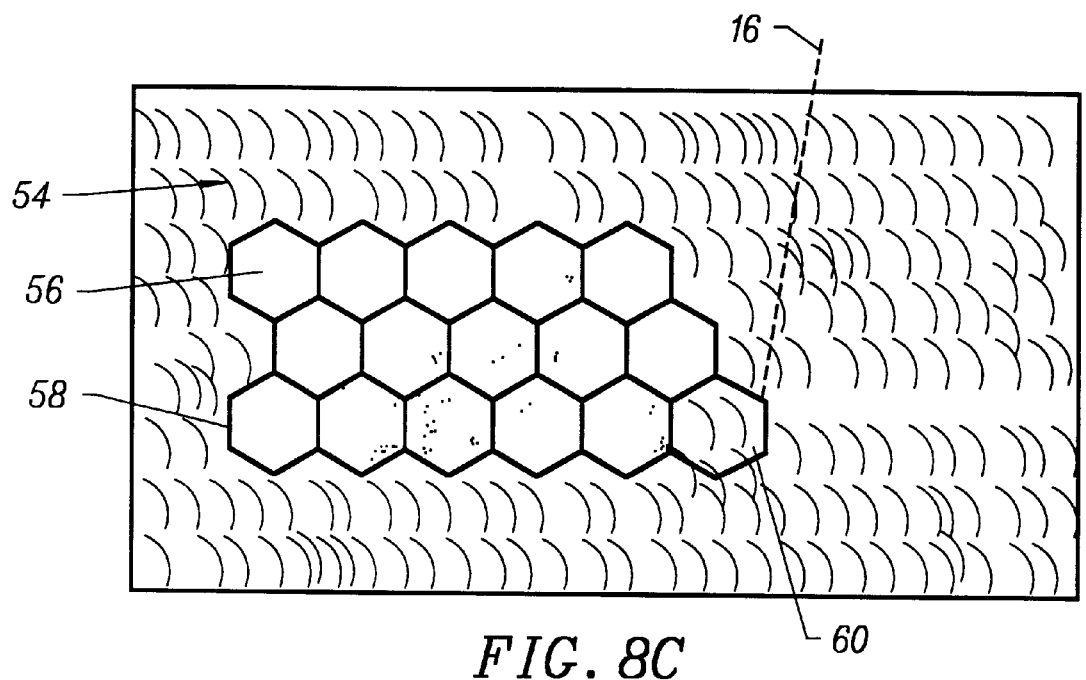
Figure 8D:
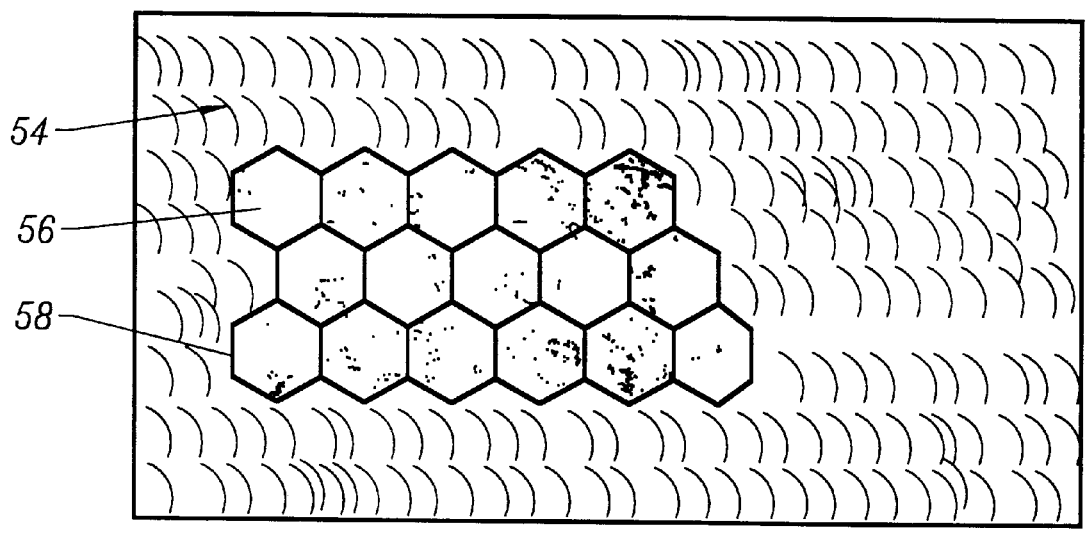

Illustrated in FIGS. 8A–D is a method for removing hair according to the present invention. As illustrated in FIG. 8A, an area of skin 52 containing hair follicles 54 is outlined. As illustrated in FIG. 8B, the area of skin 52 outlined in FIG. 8A is ablated with a laser. Areas 56 corresponds to ablated skin. The procedure illustrated in FIGS. 8A and 8B may be repeated numerous times in order to remove hair from large areas of skin. When repeating the steps illustrated in FIGS. 8A and 8B, it is generally preferred to outline and treat areas adjacent to previously treated areas. It is also generally preferred that the outlined area have a shape which is capable of forming a continuous mosaic of energy treated areas when a plurality of those shapes are laid next to each other. FIG. 8C illustrates skin which has been treated repeated times according to the steps illustrated by FIGS. 8A and 8B. As illustrated in FIG. 8C, a continuous mosaic 58 of adjacent energy treated areas 56 have been formed. Also illustrated in FIG. 8C is the step of outlining an area 60 adjacent the energy treated areas 56. FIG. 8D illustrates the step of extending the continuous mosaic of adjacent energy treated areas by ablating the area 60 outlined in FIG. 8C.

Figure 9A:
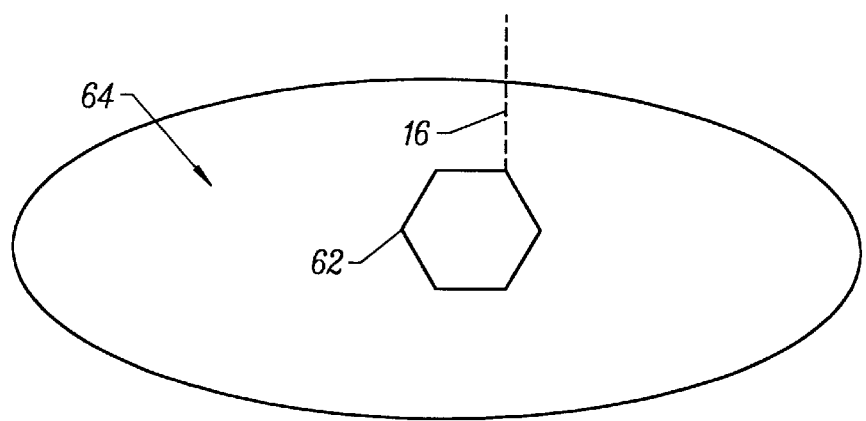
FIGS. 9A–E illustrates a method for implanting hair according to the present invention.
Figure 9B:
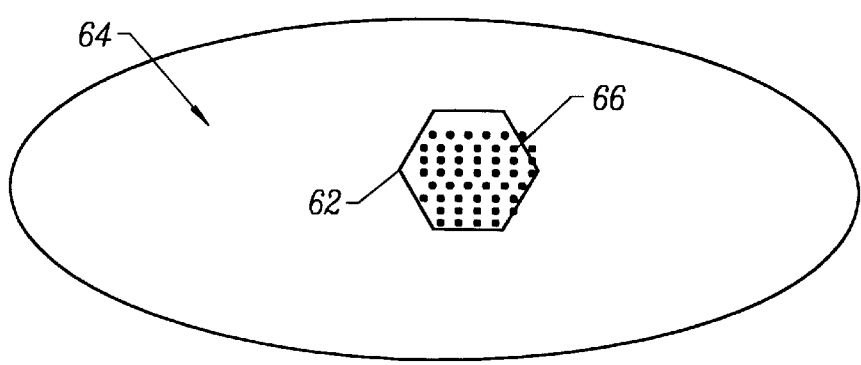
Figure 9C:
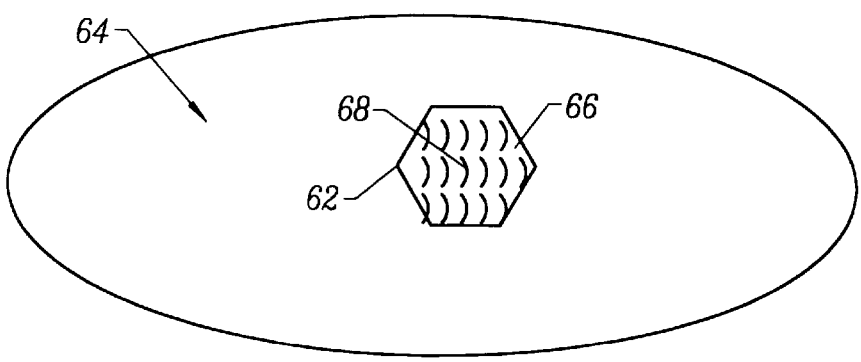

Illustrated in FIGS. 9A–E is a method for implanting hair according to the present invention. As illustrated in FIG. 9A, an area of skin 62 is outlined. As illustrated in FIG. 9B, the area of skin 62 outlined in FIG. 9A is ablated with a laser to form a series of craters into which hair follicles are implanted. Each crater should preferably be formed where the center is deeper than the edges. Areas 66 corresponds to ablated skin. As illustrated in FIG. 9C, hair follicles 68 are implanted into the ablated areas 66.

Figure 9D:
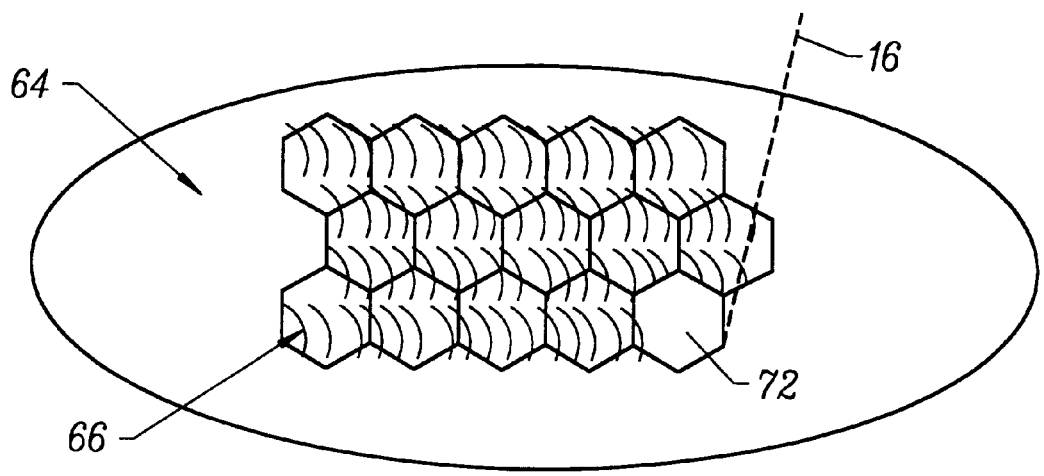
Figure 9E:
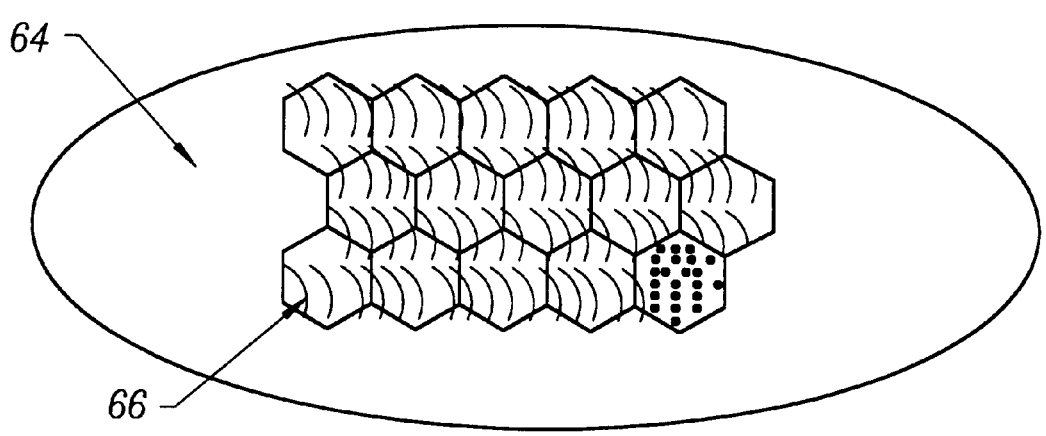

The procedure illustrated in FIGS. 9A–9C may be repeated numerous times in order to implant hair into large areas of skin. When repeating the steps illustrated in FIGS. 9A–9C, it is generally preferred to outline and treat areas adjacent to previously treated areas. It is also generally preferred that the outlined area have a shape which is capable of forming a continuous mosaic of energy treated areas when a plurality of those shapes are laid next to each other. FIG. 9D illustrates skin which has been treated repeated times according to the steps illustrated by FIGS. 9A–9C. As illustrated in FIG. 9D, a continuous mosaic 70 of adjacent energy treated areas 66 have been formed. Also illustrated in FIG. 9D is step of outlining an area 72 adjacent the energy treated areas 66. FIG. 9E illustrates the step of extending the continuous mosaic of adjacent energy treated areas by ablating the area 72 outlined in FIG. 9D.

Figure 10:
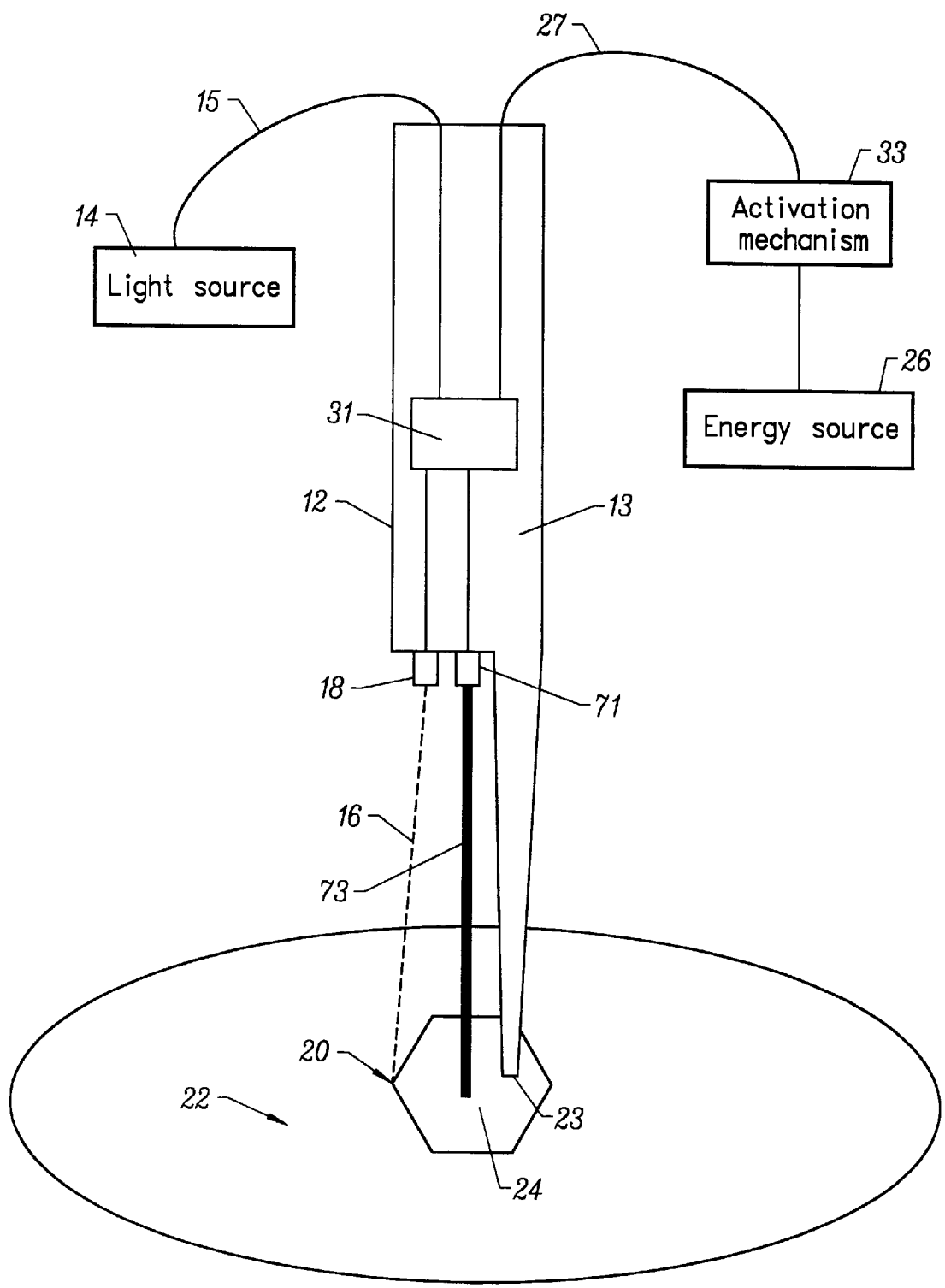
FIG. 10 illustrates an apparatus according to the present invention wherein the energy source is an Rf electrode.

FIG. 10 illustrates one embodiment of an apparatus according to the invention in which an Rf electrode 73 is used as the energy source. As illustrated in the figure, the apparatus includes a light source 14 for producing an aiming beam 16, an outlining mechanism 18 for moving the aiming beam 16 relative to a surface 22 to form a visually continuous outline 20 around an area 24 of the surface 22, an Rf electrode 73 for delivering Rf energy to the surface 22 within the outlined area 24, and an energy source direction modulator 71 which moves the Rf electrode relative to the skin to deliver Rf energy within the area 24 outlined on the surface 22.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method for delivering energy to a selected area of a surface comprising:

taking a handheld apparatus which includes an outlining mechanism and an energy source direction modulator;

placing the handheld apparatus adjacent the surface;

forming a visually continuous outline on the surface using the outlining mechanism of the handheld apparatus;

moving the handheld apparatus such that the visually continuous outline surrounds an area to be treated with energy; and delivering energy using the energy source direction modulator to the area surrounded by the visually continuous outline.

2. The method according to claim 1, wherein the visually continuous outline is produced while energy is directed to the surface.

3. The method according to claim 1, wherein the visually continuous outline has a shape, the method further including the step of selecting the shape of the visually continuous outline.

4. The method according to claim 3, wherein the shape of the visually continuous outline is selected from the group consisting of polygons, circles and ellipses.

5. The method according to claim 3, wherein the shape of the visually continuous outline is selected from the group consisting of square, diamond, rectangle, triangle, pentagon, hexagon, heptagon, and octagon.

6. The method according to claim 1, wherein the step of forming the visually continuous outline includes drawing the outline around the area to be treated with energy.

7. The method according to claim 1, wherein the visually continuous outline has a size, the method further including the step of selecting the size of the visually continuous outline.

8. The method according to claim 1, wherein the visually continuous outline has size between about 9 mm$^2$–2500 mm$^2$.

9. The method according to claim 1, wherein the visually continuous outline is formed using light from a laser.

10. The method according to claim 1, wherein the visually continuous outline and energy are formed by a same light source.

11. The method according to claim 1, wherein the energy is electromagnetic energy.

12. The method according to claim 11, wherein the electromagnetic energy is selected from the group consisting of visible light, ultraviolet light, RF energy, and microwave energy.

13. The method according to claim 1, wherein the energy is produced by a coherent light source.

14. The method according to claim 1, wherein the energy is produced by a laser.

15. The method according to claim 1, wherein the energy is focused on the surface in a spot having a diameter less than 5 mm.

16. The method according to claim 1, wherein the energy is focused on the surface in a spot having a diameter between 200 $\mu$m and 5 mm.

17. The method according to claim 1, wherein the energy is directed over substantially all of the outlined area.

18. The method according to claim 1, wherein the step of delivering energy includes delivering energy continuously within to the outlined area.

19. The method according to claim 1, wherein the step of delivering energy includes delivering energy intermittently within to the outlined area.

20. The method according to claim 1, wherein the step of delivering energy includes delivering energy in a predetermined pattern over the outlined area.

21. The method according to claim 20, wherein the predetermined pattern is adapted for performing dermoablation.

22. A method for ablating selected areas of skin on a patient comprising:

taking a handheld apparatus which includes an outlining mechanism and an energy source direction modulator;

placing the handheld apparatus adjacent the skin of the patient;

forming a visually continuous outline on the patients skin using the outlining mechanism of the handheld apparatus;

moving the handheld apparatus such that the visually continuous outline surrounds an area of skin to be ablated; and delivering energy using the energy source direction modulator to the area of skin surrounded by the visually continuous outline.

23. The method according to claim 22, wherein the energy ablates a surface layer of skin.

24. The method according to claim 23, wherein the surface layer of skin is less than about 0.05 mm thick.

25. The method according to claim 23, wherein the surface layer of skin is less than about 0.03 mm thick.

26. A method for delivering energy to a selected area of a surface comprising:

taking a handheld apparatus which includes an outlining mechanism and an energy source direction modulator;

placing the handheld apparatus adjacent the surface;

forming a visually continuous outline on the surface using the outlining mechanism of the handheld apparatus;

moving the handheld apparatus such that the visually continuous outline surrounds an area to be treated with energy; and activating an activation mechanism which causes energy to be delivered using the energy source direction modulator within the area surrounded by the visually continuous outline.

27. The method according to claim 26 where activating the activation mechanism includes continuous activation of the activation mechanism during energy delivery.

28. The method according to claim 26, wherein the activation mechanism is a footswitch, activating including depressing the footswitch.

* * * * *